United States Patent [19]

Schneider et al.

[11] Patent Number: 4,971,060

[45] Date of Patent: Nov. 20, 1990

[54] APPARATUS WORN BY A PATIENT TO PROVIDE A GEOMETRIC REFERENCE FOR MEDICAL DIAGNOSTIC DATA OBTAINED FROM THE PATIENT

[75] Inventors: Siegfried Schneider; Klaus Abraham-Fuchs, both of Erlangen, Fed. Rep. of Germany

[73] Assignee: Siemens Aktiengesellschaft, Berlin and Munich, Fed. Rep. of Germany

[21] Appl. No.: 227,305

[22] Filed: Jul. 28, 1988

[30] Foreign Application Priority Data

Jul. 30, 1987 [DE] Fed. Rep. of Germany ....... 3725325

[51] Int. Cl.$^5$ .............................................. A61B 5/05
[52] U.S. Cl. ................................................. 128/653.1
[58] Field of Search ....................... 128/653 R, 303 B; 378/38–40, 20, 63, 162, 163, 168, 208

[56] References Cited

U.S. PATENT DOCUMENTS

| | | |
|---|---|---|
| 3,577,160 | 5/1971 | White . |
| 4,228,799 | 10/1970 | Amichkov et al. ............. 128/303 B |
| 4,319,136 | 3/1982 | Jinkins . |
| 4,400,819 | 8/1983 | Bens et al. . |
| 4,400,826 | 8/1983 | Preti et al. ............................. 378/168 |
| 4,501,009 | 2/1985 | Abele ..................................... 378/4 |
| 4,618,978 | 10/1986 | Cosman .......................... 128/303 B |
| 4,714,883 | 12/1987 | Ordige ................................... 324/309 |
| 4,736,751 | 4/1988 | Gevins et al. ...................... 128/732 |
| 4,782,503 | 11/1987 | Molitor et al. ........................ 378/38 |
| 4,793,355 | 12/1988 | Crum et al. ..................... 128/653 R |

FOREIGN PATENT DOCUMENTS 0193650 9/1986 European Pat. Off. .

OTHER PUBLICATIONS

"Neuromagnetic Fields Evoked by a Patterned On–Offset Stimulus", Kouijzer et al., IEEE Transactions on Biomedical Engineering, BME-32, No. 6, June, 1985.
Zhu et al., "Accuracy of Area Measurements", *Journal of Computer Assisted Tomagraphy,* 10(1): 96–102, Jan.-Feb., 1986.

*Primary Examiner*—Ruth S. Smith
*Assistant Examiner*—John D. Zele

[57] ABSTRACT

An apparatus worn by a patient to provide a geometric reference for medical diagnostic data obtained from the patient has an element rigidly attachable to the patient, this element being connected to other components which emit a known and recognizable signal during the acquisition of medical diagnostic data, those components being used to establish a geometric reference for the data obtained from the patient. In one embodiment, a bite-down plate having a shape corresponding to the dentition of the patient is held in the mouth of the patient, and is connected to a rigid carrier having markings for geometrically referencing a tomographic image. In another embodiment, the worn element is a rigid ring worn by the patient as a headband, having a number of length-variable indicators, each of which having a scale, and also being connected to a member having a recognizable shape, or having markings, for a reference in tomographic imaging. Both embodiments can be used with other examination equipment, such as devices for obtaining biomagnetic signals, so that the respective data obtained from multiple examination devices can be geometrically correlated.

4 Claims, 3 Drawing Sheets

APPARATUS WORN BY A PATIENT TO PROVIDE A GEOMETRIC REFERENCE FOR MEDICAL DIAGNOSTIC DATA OBTAINED FROM THE PATIENT

BACKGROUND OF THE INVENTION

1. Field of the Invention

The present invention is directed to an apparatus for correlating geometric information regarding an examination subject, which are acquired in a tomographic imaging device, to measuring points which are acquired from the same examination subject in a different measuring apparatus, such as a biomagnetic measuring apparatus.

2. Description of the Prior Art

The measurement of biomagnetic signals is becoming an increasingly utilized medical diagnostic tool as described, for example, in the periodical "Bild der Wissenschaft," No. 8, 1986, pages 76-83. Extremely weak biomagnetic signals can be acquired by so-called SQUID systems. Those signals include, for example, so-called evoked magnetic fields of the human brain, which are on an order of magnitude of only $10^{-14}T$. For undertaking such a measurement, the test subject is brought into a magnetically shielded measuring room, and the patient's head is scanned in a non-contacting fashion with the SQUID system or a magnetometer. The data acquired in this manner are evaluated by a computer based on a pre-determined mathematical model. Further patient data are required, particularly data identifying the geometry of the patient, for example, identifying the structure, size and extent of the brain. The further patient data can be obtained using different examination techniques, such as ultrasound, computer tomography, or magnetic resonance imaging. It is a problem in the art to coordinate the biomagnetic test results with the results of the other imaging methods. The problem of coordination of the different signals can be further explained with reference to the example of a magneto encephalogram measurement (MEG), and a nuclear magnetic resonance tomograph image. Coordinating the data from these two measurement systems requires (a) identification of the position and orientation of the head of the patient relative to the detector array in the MEG measurement, (b) fixing the head during the MEG measurement, and (c) identification of the position and orientation of the head in the MR image relative to the position and orientation of the head in the MEG measurement, or vise versa.

Only when the above problems have been satisfactorily resolved can a point in the MR image be unambiguously coordinated to each of the measuring points of the head identified with the SQUID gradiometer. Stated in more general terms, the problem is to determine what geometrical relationship exists between the individual measuring points of the MEG measurement and the contour of the brain which is identified in a tomography imaging method, and is represented in a tomogram. Another statement of the problem is to determine the geometrical coordination of information regarding an examination subject which were acquired in a tomographic imaging apparatus relative to the measuring points which were acquired from the same examination subject in a measuring system for biomagnetic signals.

SUMMARY OF THE INVENTION

It is an object of the present invention to provide an apparatus which provides the above geometric coordination of data obtained by two different measuring systems from the same patient.

The portion of the problem discussed above identifying the position and orientation of the head of the patient relative to the planar detector array in the MEG measurement has been solved, by itself, as described in a brochure of Biomagnetic Technologies, Inc. of San Diego, Calif., dated July 1986, entitled "Probe Position Indicator." In this technique, small coils are secured to defined points of the head (for example nasion, inion or auditory canal). The magnetic field of a current flowing through one of the coils is measured, and the position of the coils, and thus the position of the defined points of the head, is calculated therefrom by inversely solving the Maxwell equations. This known solution to that portion of the problem, however, does not achieve a coordination between data obtained from two different measuring devices.

Another individual solution to one of the above portions of the problem, namely fixing the head during the MEG measurement, is described in the dissertation of C. J. Stok, Rijksuniversiteit Leiden, the Netherlands, 1986 entitled "The Inverse Problem in EEG and MEG with application to visual evoked responses", particularly page 4 and FIG. 3.4. The solution to this problem is to use a mouthpiece or bite-down plate which is held in the mouth of the examination subject. This mouthpiece or bite-down plate, however, only serves to hold the patient or subject in a prescribed position with reference to a SQUID gradiometer. Again, there is no solution suggested to coordinate the data obtained in this manner with data obtained from some other measurement device.

The entirety of the problems stated above is solved in accordance with the principles of the present invention in an apparatus worn by a patient in a manner which fixes the position of the apparatus relative to the patient, with the remainder of the apparatus being provided at various locations with markings which provide an identifiable signal for the type of measurement apparatus being used, for example, computer tomography or magnetic resonance imaging.

In a first embodiment, the apparatus includes a bite-down plate having a shape corresponding to the bite or dentition of the patient, and a rigid carrier connected, or adapted for connection, to the bite-down plate, the carrier having the aforementioned markings thereon. As used above, the term "worn" encompasses the holding of the bite-down plate in the mouth of the patient.

The rigid carrier can have an arbitrary structure, for example, a plate. The carrier may consist, for example, of plastic. A plastic plate, however, is only one, simple possibility for realizing the rigid carrier. Many other forms are conceivable, for example, an angled plate. It is also possible to provide a rigid coupling of the bite-down plate to a semi-circular band which has free ends respectively terminating at each of the auditory canals of the patient. The weight of the apparatus which must be borne by the patient holding the bite-down plate in his mouth is thus balanced, and thereby relieved.

During measurement, using the apparatus the patient holds the apparatus in place by biting on the bite-down plate, and is subjected to a tomographic imaging examination. Subsequently, the bite-down plate is rigidly connected to the measuring apparatus for obtaining the biomagnetic signals. The patient again bites on the bite-down plate, and a corresponding biomagnetic measurement is undertaken in this position. The respective sets of data obtained during the examination procedures are thus geometrically correlated to each other.

In another embodiment of the invention, the apparatus is held in place by a rigid headband or ring which is worn by the patient. A plurality of length-variable indicators, each having a scale, are attached to the ring. A member is also connected to the ring which is visibly shaped or marked so that its position and orientation in space are identifiable with the particular diagnostic procedure being used. The two measurements are then undertaken using this apparatus, as described above, with the resulting two sets of data being geometrically correlated.

In this embodiment, the visibly shaped or marked member may be an angled plate, a cross, or a circular disk.

Whereas in the first embodiment only the bite of the patient serves as a head fixing point, in the second embodiment more than one fixed point is required to bring the apparatus to a defined position relative to the head of the patient. This is accomplished by using the length-variable indicators.

DESCRIPTION OF THE PREFERRED EMBODIMENTS

Figure 1:
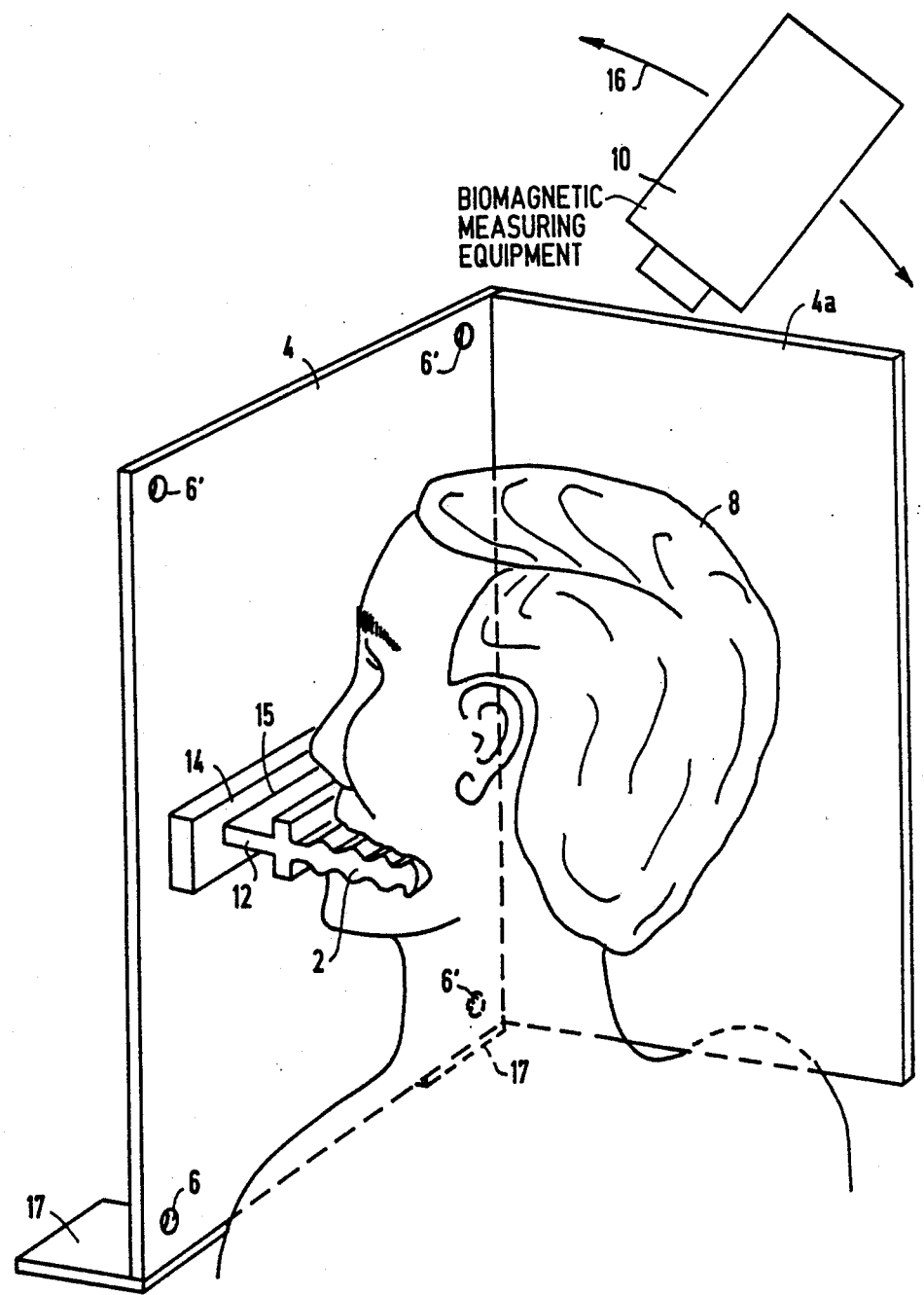
FIG. 1 is a perspective view of an apparatus constructed in accordance with the principles of the present invention being used during an examination, in a first embodiment.
Figure 2:
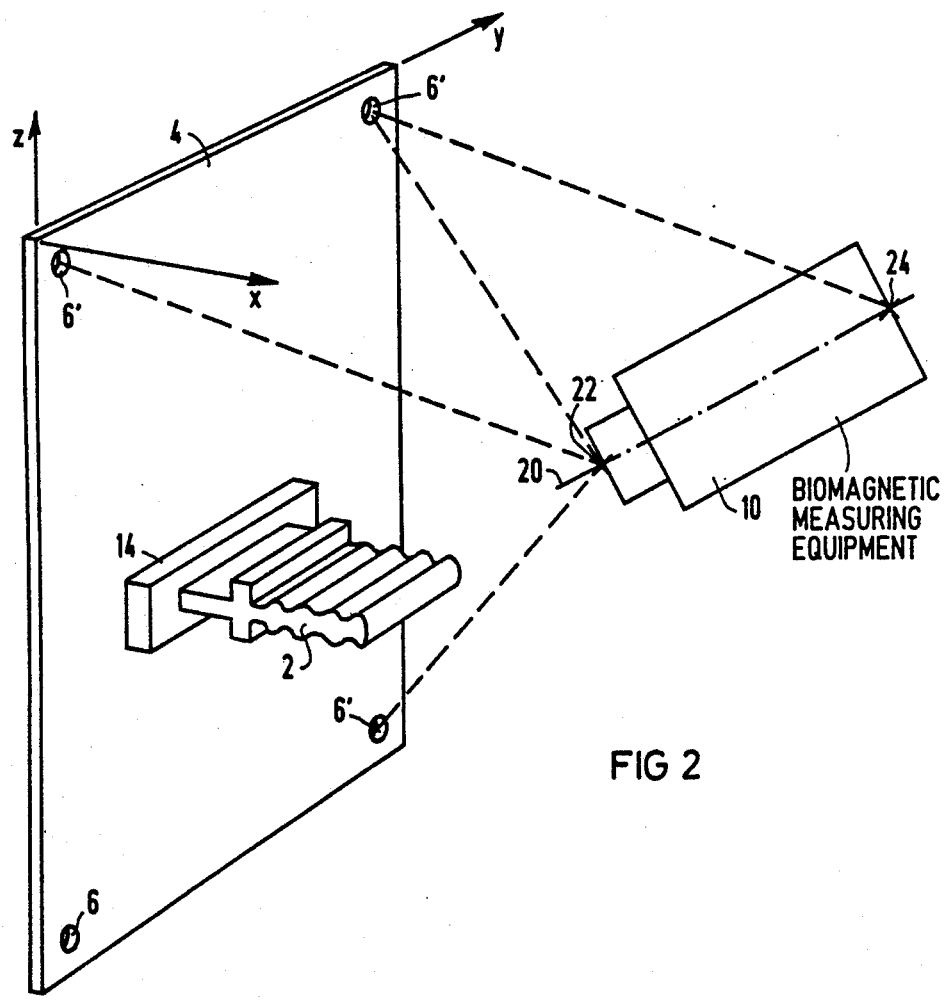
FIG. 2 is a schematic diagram showing the geometric relationships of the apparatus used in FIG. 1 with measuring equipment for obtaining biomagnetic signals.

As shown in FIGS. 1 and 2, a first embodiment of the invention includes a combination of a bite-down plate 2 and a rigid carrier 4 which is provided with markings 6 and 6'. The markings provide correlation signals, as described below. This combination is used to fix the head 8 of a patient in the identical position in two examination devices during two examination procedures. It is used, for example, first in combination with measuring equipment 10 for biomagnetic signals, and with a medical tomographic imaging apparatus (not shown). The apparatus, as described below, ensures that the same defined relationship will exist between the carrier 4 and the MEG measuring equipment as exists between the carrier 4 and the tomographic imaging measuring equipment.

The bite-down plate 2 is a negative impression of the dentition of the subject obtained by a rapidly setting compound as is employed, for example, by a dentist. When the subject bites on the bite-down plate 2, a fixed coupling between the head 8 and the bite-down plate 2 is ensured. The bite-down plate 2 can be plugged into a connector 14 of the carrier 4 via a holder 12. The connector 14 ensures a releasable, but rigid, attachment of the bite-down plate 2 and the carrier 4. The connector 14, as shown, can have a receptacle 15, reinforced at its edges, or may alternatively be in the form of a frame. The connector 14 can be reproducibly adjustable, so that it can be set at a comfortable position for the individual patient.

In the embodiment shown in FIG. 1, the carrier 4 is a plate consisting of plastic having a size, for example, of 20 cm×20 cm. In the embodiment of FIG. 1, the carrier 4 also has a side plate 4a, attached to the front plate at an angle of 90°, against which the head 8 of the patient rests at the ear. The combination of the bite-down plate 2 and the carrier 4, and, as warranted, the side plate 4a, enables both a defined positioning of the head 8 during the measurement of biomagnetic signals and a coordination of the position of the measuring equipment 10 of, for example, a SQUID gradiometer rotatable along the double arrow 16 to the head geometry, this defined positioning being visible from the tomographic image obtained during a separate measurement, for example, an MR image. For this purpose, the carrier 4 is provided with fastening elements 17, for example plug-in pins or clamps, which permit the carrier 4 to be fastened to a rigid stand (not shown) for the measuring equipment 10.

The holder 12 for the bite-down plate 2 is already integrated with the impression compound during the production of the bite-down plate 2, so that a rigid unit results. The holder 12, shown to be of oblong shape in the embodiment of FIG. 1, permits the bite-down plate 2 to be plugged into the carrier 4 via the connector 14 in a reproducible manner, i.e., the bite-down plate can be repeatedly positioned with high spatial precision. The bite-down plate 2 is produced only once for each patient, which involves little outlay, and can then be used as often as desired for that patient. The head 8 is fixed in position extremely well, because of the rigid connection between the patient's jaw bones and cranial bones. The positioning between the bite-down plate 2 and the carrier 4 can then be reliably reproduced, given a firm bite.

A tomographic imaging exposure of the head 8, for example, an MR exposure, is undertaken using the bite-down plate 2 and the carrier 4 and, as warranted, the side plate 4a. A fixing of position in the MR apparatus is not necessary. The position of the head 8 relative to the carrier 4 can be subsequently determined in the MR image, because the carrier 4 is provided with the fixed points or markings 6 and 6', which can be located in the MR image., The markings 6 and 6' may be, for example, holes in the carrier 4 filled with water. The reproducibility of the positioning can be checked very precisely and simply by two or three MR exposures.

As shown in FIG. 2, when measuring biomagnetic signals using a gradiometer (SQUID-array, Dewar mount, etc.) the carrier 4 can be fixed without problem relative to the measuring equipment 10, in which the gradiometer is contained. The exact position of the head 8, for example, relative to the gradiometer can then be measured. Even given a substantially arbitrary fastening of the carrier 4 to the measuring equipment 10, the identification of the position of the head 8 relative to the gradiometer can be accomplished using four range measurements, which can be simply and exactly undertaken. This is indicated by the dashed lines in FIG. 2. These measurements must identify the mutual position and orientation of the carrier 4 and the gradiometer axis 20. As shown in FIG. 2, measuring the range of three spaced markings 6' on the carrier 4 relative to a single marking 22 on the gradiometer, and measuring the range of two markings 22 and 24 on the gradiometer relative to one marking 6' on the carrier 4, are sufficient. The mathematical relationships to enable the position to be identified derives from basic geometric fundamentals.

In many instances, a few fixed positions of the carrier 4 will be sufficient in the MEG measurement. The position of the carrier 4 must be measured only once if the relative position of the gradiometer relative to the head 8 can be changed by moving the gradiometer mount. The gradiometer position and the gradiometer axis 20 can then read from the gradiometer mount, such as the Dewar mount (not shown).

Figure 3:
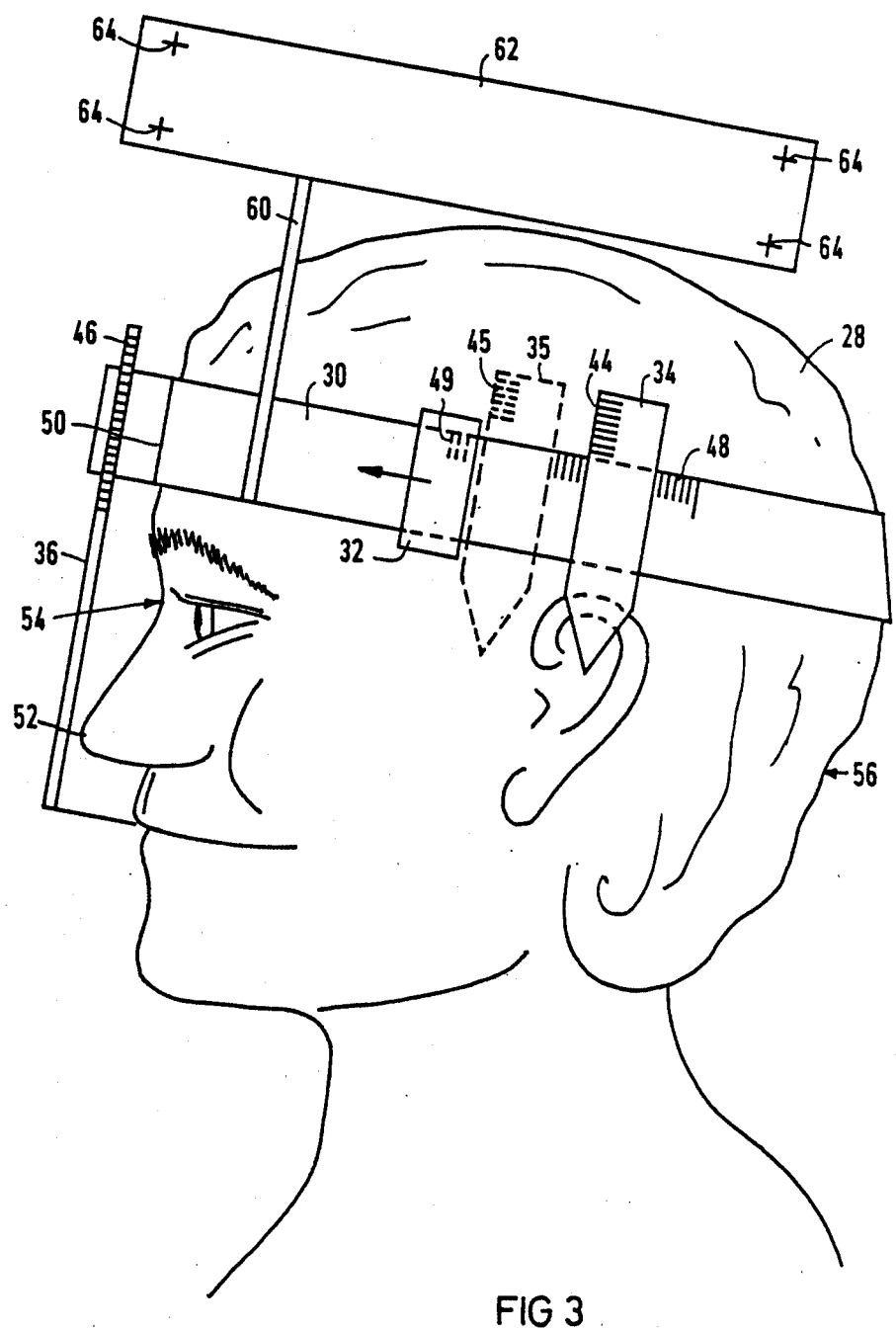
FIG. 3 is a side view of a second embodiment of an apparatus constructed in accordance with the principles of the present invention being worn by a patient.

As shown in FIG. 3, a further embodiment of the invention includes a ring or headband 30 which is rigidly worn around the head 28 of a patient. An adjustment mechanism 32 permits the headband 30 to be adapted to the head diameter, the mechanism 32 being similar, for example, to a belt buckle. Three indicators 34, 35 and 36 are mounted on the headband 30, only the indicators 34 and 36 being directly visible in FIG. 3. The indicators 34 35 and 36 are each moveable relative to the headband 30, and have respective scales 44, 45 and 46. Further scales for circular adjustment are referenced 48, 49 and 50. The indicators 34, 35 and 36 are disposed at three prominent points (fixing points) of the head 28. These points may be, for example, as shown in the embodiment of FIG. 3, the respective centers of the two auditory canals, and the center of the gap between the incisors and the upper jaw. Alternatively, the tip 52 of the nose, the nasion 54 and/or the inion 56 may serve as fixing points. There is thus a rigid correlation between the fixing points of the head 28 and the reproducibly set indicators 34, 35 and 36. The respective positions of the indicators 34, 35 and 36 are noted, and are used in the other measuring procedures.

A geometrical member is attached to the headband 30 via an adapter 60. The member 62 is rigidly connected to the headband 30 via the adapter 60. The geometrical member 62 is recognizably shaped for a predetermined tomographic imaging method and may have, for example, a plate shape, a cross shape, or a circular shape. In addition to the identifiable shape of the member 62, or instead of providing the member 62 with such a recognizable shape, the member 62 may be provided with spaced markings 64. For MR examinations, the markings 64 may be liquid-filled holes in a geometrically simple configuration, for example, a quadrangle. The markings 64 define the position and orientation of the member 62 in space, and thus also define the position of the head 28. The headband 30 is preferably a non-magnetic band. The adapter 60 permits different members 62 to be attached to the headband 30 for different patients.

For examinations of the thorax of a patient, a corresponding band is placed around the thorax. The indicators attached thereto may be applied to the mammaries and to the upper and lower end of the sternum. Other suitable fixing points may be selected.

In addition to the aforementioned examination method using nuclear magnetic resonance tomography, other examination techniques such as computer tomography, SPECT, PET and ultrasound may be used as diagnostic procedures for producing the desired tomographic image. The same apparatus can be used to correlate images obtained from any of those methods with the biomagnetic signals by using a suitable marking 64 (or 6 and 6') easily identifiable on the particular image being generated.

The apparatus disclosed herein can be used in any procedure wherein a patient is to be examined using a plurality of diagnostic methods, particularly non-contacting diagnostic methods, wherein an especially high precision with respect to the positioning and the following therapy is required.

Although modifications and changes may be suggested by those skilled in the art it is the intention of the inventors to embody within the patent warranted hereon all changes and modifications as reasonably and properly come within the scope of their contribution to the art.

We claim as our invention:

1. An apparatus for providing correlation between a first geometric position of a patient's head relative to measuring equipment of a biomagnetic signal measurement installation and a second geometric position of the patient's head relative to a tomographic imaging device, said first and second geometric positions being non-simultaneous, said apparatus comprising:
    a bite-down plate formed to match a patient's dentition so that the bite-down plate is reproducibly held in the same position in the mouth of said patient;
    a carrier element;
    means for rigidly connecting said bite-down plate to said carrier element;
    means adapted for adjustably and removably connecting said carrier element to said biomagnetic signal measurement installation; and
    at least three marks disposed on said carrier element spaced from each other and consisting of material different from the material of said carrier element and identifiable in a tomographic image.

2. An apparatus as claimed in claim 1, wherein said carrier element is planar.

3. An apparatus as claimed in claim 2, wherein said carrier element has a size of about 20 cm ×20 cm.

4. An apparatus as claimed in claim 1, wherein said marks on said carrier element are a plurality of water-filled holes in said carrier element.

* * * * *